United States Patent
Aviv et al.

(12)

(10) Patent No.: US 6,229,003 B1
(45) Date of Patent: May 8, 2001

(54) PRODUCTION OF BOVINE GROWTH HORMONE BY MICROORGANISMS

(75) Inventors: Haim Aviv, Rehovot; Eliyahu Keshet, Ramat; Marian Gorecki, Rehovot; Arie Rosner, Nes Ziona, all of (IL)

(73) Assignee: Yeda Research and Development Company Ltd., Rehovot (IL)

( * ) Notice: Subject to any disclaimer, the term of this patent is extended or adjusted under 35 U.S.C. 154(b) by 0 days.

(21) Appl. No.: 08/457,405

(22) Filed: Jun. 1, 1995

Related U.S. Application Data

(63) Continuation of application No. 08/317,248, filed on Oct. 3, 1994, now abandoned, which is a continuation of application No. 08/171,186, filed on Dec. 21, 1993, now abandoned, which is a continuation of application No. 07/891,684, filed on May 29, 1992, which is a continuation of application No. 07/646,666, filed on Jan. 28, 1991, which is a continuation of application No. 06/772,365, filed on Sep. 4, 1985, now abandoned, which is a continuation of application No. 06/568,744, filed on Jan. 6, 1984, now abandoned, which is a continuation of application No. 06/245,953, filed on Mar. 20, 1981, now abandoned.

(30) Foreign Application Priority Data

Mar. 24, 1980 (IL) ........................................ 596900

(51) Int. Cl.⁷ ........................... C12N 15/18; C12N 15/63; C12N 1/21; C07K 14/61
(52) U.S. Cl. .................. 536/23.51; 435/69.4; 435/252.8; 435/320.1; 530/399
(58) Field of Search .................................... 530/399, 300, 530/350; 536/23.1, 23.51; 435/69.1, 69.4, 320.1, 71.1, 252.8

(56) References Cited

U.S. PATENT DOCUMENTS

| | | |
|---|---|---|
| 2,370,154 | 2/1945 | Fleischer et al. . |
| 3,886,132 | 5/1975 | Brewer et al. .................... 260/112.5 |
| 4,010,148 | 3/1977 | Goldstein ............................ 260/112 |
| 4,342,832 * | 8/1982 | Goeddel et al. ..................... 435/172 |

FOREIGN PATENT DOCUMENTS

| | | |
|---|---|---|
| 2535554 | 8/1974 | (DE) . |
| 0012494 | 8/1979 | (EP) . |
| 1568047 | 5/1978 | (GB) . |

OTHER PUBLICATIONS

Seeburg et al., Nature 276:795–798 (1978).
Lingappa et al., Cell Biol. 74:2432–2436 (1977).
Cohen et al., P.N.A.S. 70 (11):3240–3244 (1973); and.
Chang et al., P.N.A.S. 71 (4):1030–1034 (1974).
Nilson et al. (1979), "Purificatio of Pre–prolactin mRNA from Bovine Anterior Pituitary Glands", J. Biol. Chem. 254:1516–1520.
Keiichi Itakura and Arthur D. Riggs (1980), "Chemical DNA Synthesis and Recombinant DNA Studies", Science 209:1401–1405.
Hunt and Dayhoff (1976), Atlas of Protein Sequence and Structure, (National Biomed. Res. Fund.) Washington, D.C., vol. 5, Supp. 2, p. 11.
Edge et al. (1981), "Total Synthesis Of A Human Leukocyte Interferon Gene", Nature 292:756–762.
Coutelle et al. (1978), "Use of Matrix–Immobilised Recombinant Plasmids To Purify Chain–Specific Rabbit Globin Complementary DNAs", Gene 3:113–122.
Sassavage et al., Federation Proceedings, Abstracts, (1979), 38:398.
Miller et al. (1980), "Molecular Cloning of DNA Complementary to Bovine Growth Hormone mRNA", J. Biol. Chem. 255:7521–7524; and.
Goeddel et al. (1979), "Direct Expression In *Escherichia coli* Of A DNA Sequence Coding For Human Growth Hormone", Nature 281:544–548.
Seeberg et al 1977 Nature 270:486–494.*
Wallis et al 1973 FEBS Lett 35(1):11–14.*
Martial et al 1979 Science 205:602–607.*
Miller et al 1980 J Biol Chem 255(16):7521–7524.*

* cited by examiner

*Primary Examiner*—Christine Saoud
(74) *Attorney, Agent, or Firm*—John P. White; Cooper & Dunham LLP

(57) ABSTRACT

The present invention relates to strains of *E coli* adapted to produce bovine growth hormone, being the result of extraction of RNA from bovine pituitaries, transcription of DNA on such RNA templates, splicing of DNA into plasmids, insertion of spliced plasmid into microorganisms, and further subjecting the microorganisms to selection and isolating the colonies producing the desired fused or modified growth hormone and to modified bovine growth hormone obtained by the cultivation of such modified *E. coli* strains and recovery of the desired product.

8 Claims, 2 Drawing Sheets

FIGURE 1A

```
            10           20           30           40           50
             *            *            *            *            *
GG GGG GGG GGG GCT GCA GGC CCC CGG ACC TCC CTG CTC CTG GCT TTC GCC CTG
                Ala Ala Gly Pro Arg Thr Ser Leu Leu Leu Ala Phe Ala Leu 60           70           80           90          100
             *            *            *            *            *
CTC TGC CTG CCC TGG ACT CAG GTG GTG GGC GCC TTC CCA GCC ATG TCC TTG TCC
Leu Cys Leu Pro Trp Thr Gln Val Val Gly Ala Phe Pro Ala Met Ser Leu Se 110          120          130          140          150          160
             *            *            *            *            *            *
GGC CTG TTT GCC AAC GCT GTG CTC CGG GCT CAG CAC CTG CAC CAG CTG GCT GCT
Gly Leu Phe Ala Asn Ala Val Leu Arg Ala Gln His Leu His Gln Leu Ala Ala 170          180          190          200          210
             *            *            *            *            *
GAC ACC TTC AAA GAG TTT GAG CGA ACC TAC ATC CCG GAG GGA CAG AGA TAC TCC
Asp Thr Phe Lys Glu Phe Glu Arg Thr Tyr Ile Pro Glu Gly Gln Arg Tyr Ser 220          230          240          250          260
             *            *            *            *            *
ATC CAG AAC ACC CAG GTT GCC TTC TGC TTC TCT GAA ACC ATC CCG GCC CCC ACG
Ile Gln Asn Thr Gln Val Ala Phe Cys Phe Ser Glu Thr Ile Pro Ala Pro Thr 270          280          290          300          310          320
   *            *            *            *            *            *
GGC AAG AAT GAG GCC CAG CAG AAA TCA GAC TTG GAG CTG CTT CGC ATC TCA CTG
Gly Lys Asn Glu Ala Gln Gln Lys Ser Asp Leu Glu Leu Leu Arg Ile Ser Le 330          340          350          360          370
             *            *            *            *            *
CTC CTC ATC CAG TCG TGG CTT GGG CCC CTG CAG TTC CTC AGC AGA GTC TTC ACC
Leu Leu Ile Gln Ser Trp Leu Gly Pro Leu Gln Phe Leu Ser Arg Val Phe Thr 380          390          400          410          420          430
   *            *            *            *            *            *
AAC AGC TTG GTG TTT GGC ACC TCG GAC CGT GTC TAT GAG AAG CTG AAG GAC CTG
Asn Ser Leu Val Phe Gly Thr Ser Asp Arg Val Tyr Glu Lys Leu Lys Asp Leu
```

FIGURE 1B

```
          440            450            460            470            480
           *              *              *              *              *
GAG GAA GGC ATC CTG GCC CTG ATG CGG GAG CTG GAA GAT GGC ACC CCC CGG GCT
Glu Glu Gly Ile Leu Ala Leu Met Arg Glu Leu Glu Asp Gly Thr Pro Arg Ala 490            500            510            520            530
           *              *              *              *              *
GGG CAG ATC CTC AAG CAG ACC TAT GAC AAA TTT GAC ACA AAC ATG CGC AGT GAC
Gly Gln Ile Leu Lys Gln Thr Tyr Asp Lys Phe Asp Thr Asn Met Arg Ser Asp 540            550            560            570            580            590
  *              *              *              *              *              *
GAC GCG CTG CTC AAG AAC TAC GGT CTG CTC TCC TGC TTC CGG AAG GAC CTG CAT
Asp Ala Leu Leu Lys Asn Tyr Gly Leu Leu Ser Cys Phe Arg Lys Asp Leu His 600            610            620            630            640
           *              *              *              *              *
AAG ACG GAG ACG TAC CTG AGG GTC ATG AAG TGC CGC CGC TTC GGG GAG GCC AGC
Lys Thr Glu Thr Tyr Leu Arg Val Met Lys Cys Arg Arg Phe Gly Glu Ala Ser 650            660            670            680            690            700
  *              *              *              *              *              *
TGT GCC TTC TAG TTG CCA GCC ATC TGT TGT TTG CCC CTC CCC CGT GCC TTC CTT
Cys Ala Phe —

710            720            730            740            750
           *              *              *              *              *
GAG CCT GGA AGG TGC CAC TCC CAC TGT CCT TTC CTA ATA AAA TGA GGA AAT TGC 760            770            780            790            800
           *              *              *              *              *
ATC GCA AAA AAA AAA AAA AAA AAA AAC CCC CCC CCC CCT GCA GT
```

PRODUCTION OF BOVINE GROWTH HORMONE BY MICROORGANISMS

This application is a continuation of U.S. Ser. No. 08/317,248, filed Oct. 3, 1994, now abandoned, which is a continuation of U.S. Ser. No. 08/171,186, filed Dec. 21, 1993, now abandoned, which is a continuation of U.S. Ser. No. 07/891,684, filed May 29, 1992, which is a continuation of U.S. Ser. No. 07/646,666, filed Jan. 28, 1991, which is a continuation of U.S. Ser. No. 06/772,365, filed Sep. 4, 1985, now abandoned, which is a continuation of U.S. Ser. No. 06/568,744, filed Jan. 6, 1984, now abandoned, which is a continuation of U.S. Ser. No. 06/245,953, filed Mar. 20, 1981, now abandoned, claiming priority of Israeli patent application No. 59690, filed Mar. 24, 1980.

FIELD OF INVENTION

The invention relates to novel modified microorganisms adapted to produce a polypeptide which has the bovine growth hormone amino-acid sequence. The invention further relates to a method for the modification of easily cultivable non-pathogenic microorganisms so as to convert same to effective producers of bovine growth hormone containing polypeptide.

The invention further relates to the production of bovine growth hormone by means of easily cultivable non-pathogenic microorganisms.

BACKGROUND OF THE INVENTION

DNA which has the capacity to code for polypeptides, can be synthesized and spliced into plasmid DNA and then when cells are transformed by this recombinant DNA, the synthetic DNA will replicate in these cells. If properly inserted in phase with a suitable bacterial promoter, the synthetic DNA will be decoded (expressed) into the authentic polypeptide. The technique can be used for the production of various hormones, enzymes and other polypeptides. In each case the technique has to be adapted to the specific circumstances.

SUMMARY OF THE INVENTION

The present invention relates to novel modified microorganisms adapted to produce bovine growth hormone. The invention further relates to a process for the production of bovine growth hormone by the cultivation of such novel microorganisms. The invention further relates to the production of bovine growth hormone which comprises extracting RNA from bovine pituitaries, transcribing double-stranded DNA on these RNA templates after tailing the DNA with oligo-deoxycytidine, ligating the tailed plasmid DNA, selecting bacteria colonies containing the recombinant plasmids and cultivating said colonies to obtain a culture of cells containing the desired polypeptide and extracting same from such cultures.

According to a preferred embodiment of the invention, there are provided modified *E. coli* strains adapted to produce the desired growth hormone. Preferably, the strain used is one derived from *E. coli* HB101, and a preferred plasmid used is pBR322.

DNA was synthesized enzymatically on mRNA isolated from bovine pituitaries. The DNA was spliced into the beta-lactamase gene of a commonly used plasmid, pBR322. *E. coli* cells, preferably of the BB101 strain, or of similar strains, were transformed by the recombinant plasmids and colonies containing these plasmids were isolated. Colonies (clones) containing the coding capacity for bovine growth hormone and colonies containing the coding capacity for prolactin were identified by DNA sequencing. The inserted DNA from a colony containing the full length coding sequences for growth hormone was isolated and reinserted into another plasmid in a position adjacent to the beta-galactosidase promoter. Several colonies producing a polypeptide, which was characterized to be the desired growth hormone by gel electrophoresis and by precipitation with antiserum raised in response to pure authentic bovine growth hormone were isolated.

Procedure Used for the Construction of the Bacterial Strain which has the Capacity to Produce the Bovine Growth Hormone Fused to a Beta-lactamase Fraction RNA from a pool of several calf pituitary glands was extracted by phenol and the poly(A)-containing RNA purified by chromatography on oligo(dT)-cellulose. The poly (A)+RNA was transcribed into double-stranded DNA by reverse transcriptase (AMV). The DNA was treated with single-stranded specific nuclease (S1) and dC-tailed by terminal transferase (PL Biochemicals) and then separated by electrophoresis on an agarose gel. The higher molecular weight fraction above 500 base-pairs was isolated and annealed to dG-tailed Pst 1 cut PBR322 plasmid DNA which was prepared by the standard procedure. Ca++ treated *E. coli* HB101 was exposed to this DNA preparation. Tetracycline resistant colonies were isolated and screened for recombinant plasmids by in situ hybridization with $^{32}$P-labeled cDNA reverse transcribed from the poly(A)$^+$ RNA fraction mentioned above. Positive colonies were isolated and further screened for plasmids containing DNA sequences corresponding to bovine prolactin and growth hormone in the following way: Plasmids were prepared from each colony, the DNA was immobilized onto nitrocellulose filters and hybridized to Poly(A)$^+$ RNA extracted from pituitaries. The hybridized RNA was analyzed by its capacity to elicit the synthesis of a specific band corresponding to bovine growth hormone in a cell-free translation system. Most of the colonies were thus identified to contain DNA sequences coding for prolactin; a few have been identified to contain DNA coding for growth hormone. This was confirmed by determination on the part of the DNA sequences in an example from each group. The capacity to synthesize a polypeptide corresponding to growth hormone was analyzed by immunological techniques in the following way: The cells were labelled with $^{35}$S-methionine for 30 minutes and the proteins extracted, then incubated with an antiserum raised against purified bovine growth hormone, followed by incubation with chloroform treated Staphilococcus A. The precipitated antibody-antigen complex was then dissociated by sodium dodecysulfate, beta-mercaptoethanol and analyzed by gel electrophoresis. Several colonies were found to synthesize a polypeptide which specifically reacted with this anti-serum. The size of the growth hormone polypeptide varied; in one strain the main polypeptide was about 40K dalton, in another strain its size was about 25K. The amount synthesized in a liter fermentation vessel was determined by radioimmunoassay as described below. The strain producing the highest yield of bovine growth hormone polypeptide was designated strain $D_4$, deposited in the American Type Culture Collection, Rockville, Md., as ATCC No. 31826.

DNA Splicing to Obtain a Series of Modified Bovine Growth Hormones construction of plasmids which produce modified bovine growth hormone (bGH) in bacteria *E. coli* is presented.

All constructions are based on the DNA fragment obtained from the DNA of pBR322 plasmid that harbors the DNA for bGH, i.e., the DNA from strain $D_4$. The fragment is generated by cleavage of this plasmid obtained from strain $D_4$ with Hae II restriction endonuclease and will be designated fragment I. Fragment I comprising 1640 base pairs starts with the nucleotide No. 3 encoding the mature bGH, continues through all sequences.of bGH DNA including termination codon, then traverses through pBR322 DNA sequences from nucleotide 3612 through 2721 according to the published sequence of Sutcliffe (1978) Nucleic Acid Res 5, 2721. Therefore the beginning of fragment I is as follows:

```
          Phe²  Pro³  Ala⁴  Met⁵
     C    TTC   CCA   GCC   ATG......
   CGCGG  AAG   GGT   CGG   TAC......
``` and is missing two nucleotides necessary to encode the first amino-acid Ala.

EXAMPLE 1

Preparation of bGH starting with (Met) Pro Phe² Pro³

(1) Protruding 3' ends of fragment I are trimmed with S1 exonuclease generate DNA—Fragment II with initial sequence of

```
          C TTC CCA.....
          G AAG GGT.....
```

(2) Fragment II is ligated to EcoRl, linkers with structure
GGAATTCC
CCTTAAGG
to give fragment III as follows:

```
     GGAATTCCCTTCCCA..........GGAATTCC
     CCTTAAGGGAAGGGT..........CCTTAAGG
```

(3) Fragment III is digested with EcoRl restriction endonuclease to give fragment IV as follows:

```
          AATTCCCTTCCCA..........GG
              GGGAAGGGT..........CCAATT
```

(4) Fragment IV is ligated with EcoRl cleaved pBR322 and cloned in *E. coli* strain HB101. This new plasmid contains an insert of fragment IV which is subsequently removed with EcoRl restriction endonuclease.

(5) Fragment IV is trimmed with $S_1$ exonuclease to generate flush ended fragment V with sequence

```
             CCC TTC CCA......
             GGG AAG GGT......
```

(6) Fragment V is ligated to EcoRl-ATG linkers with structure
CATGAATTCATG
GTACTTAAGTAC
to give it fragment VI as depicted

```
          CATGAATTCATGCCCTTCCCA......
```

```
          GTACTTAAGTACGGGAAGGGT......
          ......CATGAATTCATG
          ......GTACTTAAGTAC
```

(7) In the way analogous to preparation of fragment V, fragment VI is cleaved with EcoRl and trimmed with $S_1$ exonuclease as in 1(4) and 1(5) to give fragment VII

```
          CATGCCCTTCCA............CATG
          GTACGGGAAGGT............GTAC
```

(8) Fragment VII is ligated to a lac promotor-containing pBR322 plasmid DNA (PLA II) opened with PvuII restriction endonuclease. This plasmid contains lac promoter in position fit to obtain an expression of any DNA containing ATG initiator sequences and preceeded by two nucleotides, if introduced into PvuII restriction site, and is obtained in the following way. pBR322 DNA fragment containing Ampr gene excised with EcoRl, and PvuII ligated with a 95 base pair fragment derived from Alu 1 digestion of pLJ 3 (L. Johnsrude and W. Gilbert, Proc. Natl. Acad. Sci. U.S.A. 75, 5314 (1978)). Thus the transformation of *E. coli* with the ligation mixture will generate a plasmid which will highly express modified bGH with the sequence starting with Met Pro Phe Pro This protein differs from the mature protein in that Met Pro replaces Ala of mature protein. Met can be processed by bacteria to give modified bGH starting with the amino acid sequence Pro Phe Pro. The producing strain was designated BGH1.

EXAMPLE 2

Production of (Met) Leu Gly Phe² Pro³-bGH (1) Fragment I, trimmed with exonuclease $S_1$ is ligated with Hind III linkers with structure

```
             CCAAGCTTGG......
             GGTTCGAACC......
``` to obtain fragment VIII with structure

```
             CCAAGCTTGGCTTC......
             GGTTCGAACCGAAG......
```

(2) Fragment VIII is cleaved with Hind III to give fragment IX with structure

```
             AGCTTGGCTTC......
                 ACCGAAG..........
```

(3) Fragment IX is partially filled in with polymerase I using dG and dA only. Simultaneously, the first two nucleotides of fragment IX are cleaved off to obtain fragment X with structure

```
             CTTGGCTTC.....
             GAACCGAAG.....
```

Fragment X is coupled with EcoRl-ATG linkers (as in 1(5)) and cleaved with EcoRl (as in 1(4)) and trimmed with S1 (as in 1(5)) to obtain fragment XI with structure

```
CATGCTTGGCTTC.....

GTACGAACCGAAG.....
```

(4) Fragment XI is introduced into PLA 11 (as in 1(8)) to express modified bGH with initial sequence (Met) Leu Gly Phe Pro......

The producing strain was designed bGH3.

EXAMPLE 3
Production of des (Ala$^1$ Phe$^2$ Pro$^3$ Ala$^4$)bGH. ie. bGR Starting at Met$^5$ (1) Fragment I is treated with S1 exonuclease, exonuclease III and again with S1 exonuclease. These treatments will generate a variety of flush end fragments which lead to the production of modified bGH when ligated to the last promoter at the PvuII site of PLA 11 (as in 1(8)). The subsequent treatment of fragment I with exonuclease I and S1 brings about the expression of des (Ala$^1$ Phe$^2$ Pro$^3$ Ala$^4$ bGH, i.e. a bGH starting at Met$^5$. The producing strain was designated bGH4.

EXAMPLE 4
Production of Bovine Growth Hormone-like Polypeptides by Bacteria

Ten ml of an overnight culture of a producing clone was diluted into 1 liter of sterile medium which contained 10 g Bacto-Triptone (Difco), 5 g yeast extract (Difco), 5 g sodium chloride and 10 g glucose. The culture grown at 37° C., with vigorous agitation and aeration, was harvested at mid log (1.5 $A_{600}$) after rapid chilling, by centrifugation at 7000 rpm (Sorvall) for 10 minutes. When the cells were harvested at the beginning of the stationary phase, the amount of hormone per culture (and per cell) diminished significantly. The pelleted cells were washed and then suspended in a small volume of a solution containing 20% sucrose and 2mM EDTA after 5 minutes on ice; 10 mg lysozyme was added and left for incubation for another 30 minutes. Protoplasts were thus formed. To 100 ml of protoplast extract, 1 g of barbital-Tris buffer pH 8.8 (Gelman) was added followed by Triton and Na-Sarkosyl (final 0.1%). The viscous lysate was sonicated (1 minute 50% output-Branson) to reduce viscosity. The extract was centrifuged 15000 rpm (Sorvall) for 15 minutes and the supernatant was spun 40,000 rpm (Spinco R40) for 60 minutes in order to remove the ribosomes. Most of the activity was in the supernatant. This culture produced 150 g of immunologically active fused bovine growth hormone polypeptide. Most of the hormone could be precipitated at 30% of saturation ammonium sulfate.

The amount of hormone produced was measured by radio-immunoassay i.e., by the ability to compete with radio-labelled [$^{125}$I]-pure bovine growth hormone in an immunological reaction with antiserum raised in rabbits against pure bovine growth hormone.

EXAMPLE 6
DNA Sequence of the D4 BGH Gene

To sequence the bGH gene, DNA was purified from *E. coli* strain D4, (ATCC Deposit No. 31826).

Sequencing was performed using oligodeoxyribonucleotides as primers for the dideoxy chain termination sequencing method and other well known methods of sequencing known to those skilled in the art. Sanger et. al. Proc. Nat. Acad. Sci. USA 74: 5463–5467 (1977).

The complete sequence of the bGH gene as derived by these methods is shown in FIGS. 1A and 1B.

What is claimed is:

1. An isolated DNA encoding bovine growth hormone and comprising the coding sequence:

TTC CCA GCC ATG TCC TTG TCC GGC CTG TTT GCC AAC GCT GTG CTC CGG GCT CAG CAC CTG CAC CAG CTG GCT GCT GAC ACC TTC AAA GAG TTT GAG CGC ACC TAC ATC CCG GAG GGA CAG AGA TAC TCC ATC CAG AAC ACC CAG GTT GCC TTC TGC TTC TCT GAA ACC ATC CCG GCC CCC ACG GGC AAG AAT GAG GCC CAG CAG AAA TCA GAC TTG GAG CTG CTT CGC ATC TCA CTG CTC CTC ATC CAG TCG TGG CTT GGG CCC CTG CAG TTT CTC AGC AGA GTC TTC ACC AAC AGC TTG GTG TTT GGC ACC TCG GAC CGT GTC TAT GAG AAG CTG AAG GAC CTG GAG GAA GGC ATC CTG GCC CTG ATG CGG GAG CTG GAA GAT GGC ACC CCC CGG GCT GGG CAG ATC CTC AAG CAG ACC TAT GAC AAA TTT GAC ACA AAC ATG CGC AGT GAC GAC GCG CTG CTC AAG AAC TAC GGT CTG CTC TCC TGC TTC CGG AAG GAC CTG CAT AAG ACG GAG ACG TAC CTG AGG GTC ATG AAG TGC CGC CGC TTC GGG GAG GCC AGC TGT GCC TTC TAG.

2. DNA encoding bovine growth hormone having the coding sequence from nucleotide 87 to nucleotide 659 of FIGS. 1A and 1B.

3. A plasmid comprising the DNA of claim 1.

4. A plasmid comprising the DNA of claim 2.

5. An *Escherichia coli* strain containing the plasmid of claim 3.

6. An *Escherichia coli* strain containing the plasmid of claim 4.

7. An *Escherichia coli* strain according to claim 5 designated D4 and deposited under ATCC Accession No. 31826.

8. An *Escherichia coli* strain according to claim 6 designated D4 and deposited under ATCC Accession No. 31826.

* * * * *